(12) United States Patent
Chen

(10) Patent No.: US 8,060,191 B2
(45) Date of Patent: Nov. 15, 2011

(54) WIRELESS CARDIOGRAM SIGNAL DIAGNOSTIC INSTRUMENT

(75) Inventor: Tong-Pie Chen, Sanchung (TW)

(73) Assignee: Zentan Technology Co., Ltd., Sanchung (TW)

( * ) Notice: Subject to any disclaimer, the term of this patent is extended or adjusted under 35 U.S.C. 154(b) by 401 days.

(21) Appl. No.: 12/396,734

(22) Filed: Mar. 3, 2009

(65) Prior Publication Data

US 2010/0036270 A1 Feb. 11, 2010

(30) Foreign Application Priority Data

Aug. 8, 2008 (TW) ................................ 97214235 U

(51) Int. Cl.
*A61B 5/0402* (2006.01)
*A61B 5/0416* (2006.01)
*A61B 5/044* (2006.01)

(52) U.S. Cl. .................. 600/509; 600/390; 600/523

(58) Field of Classification Search .................. 600/509, 600/520, 523, 384, 386, 390, 393
See application file for complete search history.

(56) References Cited

U.S. PATENT DOCUMENTS

| | | | |
|---|---|---|---|
| 7,039,456 B2 * | 5/2006 | Chen | 600/509 |
| 7,330,751 B2 * | 2/2008 | Ueda | 600/509 |
| 2006/0058695 A1 * | 3/2006 | Chen | 600/509 |
| 2006/0149158 A1 * | 7/2006 | Fujii et al. | 600/519 |

* cited by examiner

*Primary Examiner* — Carl H. Layno
*Assistant Examiner* — Tammie K Heller
(74) *Attorney, Agent, or Firm* — C. G. Mersereau; Nikolai & Mersereau, P.A.

(57) ABSTRACT

A wireless cardiogram signal diagnostic instrument includes a band, a signal transmitting device, two sets of connecting pieces, and a conductive assembly. The band has two opposite mounting portions separated by a distance. The two mounting portions are provided with the conductive assembly having a first conductive piece and a second conductive piece. The signal transmitting device is provided with a third conductive piece. The two sets of connecting pieces each have a first connecting piece that is conductive provided on the mounting portion of the band and a second connecting piece that is conductive provided on the signal transmitting device. The first connecting piece is correspondingly assembled with the second connecting piece, so that the signal transmitting device can be detachably assembled on the band. Via the above arrangement, the instrument can be worn on a user's chest to collect and measure the variation values of cardiogram voltages.

9 Claims, 4 Drawing Sheets

WIRELESS CARDIOGRAM SIGNAL DIAGNOSTIC INSTRUMENT

BACKGROUND OF THE INVENTION

1. Field of the Invention

The present invention relates to a physiological signal diagnostic instrument, and in particular to a wireless cardiogram signal diagnostic instrument for detecting variation values of cardiogram voltages.

2. Description of Related Art

Since the cardiogram signals generated by a human body have a close relation relationship with his/her health conditions, the function of one's body can be understood by means of detecting his/her cardiogram signals. Therefore, various kinds of instruments for measuring cardiogram signals have been developed, whereby the cardiogram signals of one's body can be detected so as to monitor his/her health conditions.

For example, a medical cardiogram device is provided with a plurality of electrode patches and leads. A user attaches the electrode patches to a human body, and then connects the leads between the electrode patches and a computer device. Via this arrangement, the cardiogram signals detected by the electrode patches are transmitted to the computer device. Subsequently, the computer device stores, analyzes and displays the received cardiogram signals.

If there is a problem in one's heart, he/she may have to go to the hospital merely to perform a cardiogram examination, which leads to significant expense; furthermore, it is impossible for one to measure and monitor his/her cardiogram conveniently at a more continuous basis since the equipment is stationed at the hospital. However, portable medical instruments are currently available on the market, such as wireless heartbeat transmitter transmitters for measuring one's pulse, and are usually provided with a sensing band on both sides. Conductive material on the sensing band is used for sensing signals of a human body. Yet, the signals of a human body may be collected insufficiently and some signals may even be lost. As a result, the accuracy in measuring signals of a human body is not enough.

Consequently, because of the above limitation resulting from the technical design of prior art, the inventor strives via real world experience and academic research to develop the present invention, which can effectively improve the limitations described above.

SUMMARY OF THE INVENTION

The object of the present invention is to provide a wireless cardiogram signal diagnostic instrument, which can be worn on the user's chest to be positioned in close proximity to his/her heart so as to thereby measure and collect accurate variation values cardiogram voltages. Then, the collected cardiogram signals are processed and transmitted by a signal transmitting device. Thereafter, the transmitted signals are received by a receiver, thereby displaying a cardiogram or recording the collected cardiogram signals. Via this arrangement, the user can monitor his/her cardiogram, thereby overcoming the drawback that the signals of a human body may be collected insufficiently or even lost.

In order to achieve the above objects, the present invention provides a wireless cardiogram signal diagnostic instrument, which comprises: a band having a first surface and a second surface opposite to each other, and having two opposite mounting portions separated by a distance; a signal transmitting device having an outer casing, wherein a circuit board is provided in the outer casing. Therein, a signal transmitting element, an arithmetic processing element, a first electrode, a second electrode, and a third electrode are electrically connected to the circuit board. The outer casing further having a third surface and a fourth surface opposite to each other, the third surface of the outer casing being oriented in the same direction as the first surface of the band, the fourth surface of the outer casing being oriented in the same direction as the second surface of the band; two sets of connecting pieces each having a first connecting piece and a second connecting piece that are conductive, the first connecting pieces being provided on the two mounting portions of the band and are electrically coupled to the corresponding first and second conductive pieces respectively, the second connecting pieces being provided on the outer casing of the signal transmitting device and are electrically coupled to the corresponding first and second electrodes respectively, the first connecting pieces being assembled with the corresponding second connecting pieces, so that the signal transmitting device is detachably assembled on the second surface of the band; and a conductive assembly having a first conductive piece, a second conductive piece, and a third conductive piece, the first and second conductive pieces being nakedly provided on the first surfaces of two mounting portions of the band, the third conductive piece being nakedly provided between the first surfaces of the band and the third surface of the outer casing with the third conductive piece being located between the two mounting portions, and the third conductive piece and the third electrode being electrically coupled to each other.

The present invention has advantageous features as follows. The present invention can be worn on the user's chest with the first to third conductive pieces being attached to the user's skin, thereby located in close proximity to the user's heart so as to collect accurate variation values of cardiogram voltages. Then, the collected values are processed by the signal transmitting device and transmitted to a receiver. The transmitted signals are received by the receiver to display the cardiogram or record the collected cardiogram signals. Therefore, it is convenient for the user to monitor his/her cardiogram. Further, the drawback that the signals of a human body may be collected insufficiently or even lost can be solved.

In order to further understand the characteristics and technical contents of the present invention, a detailed description relating thereto will be made with reference to the accompanying drawings. However, the drawings are illustrative only, but not used to limit the scope of the present invention.

DETAILED DESCRIPTION OF THE PREFERRED EMBODIMENTS

Figure 1:
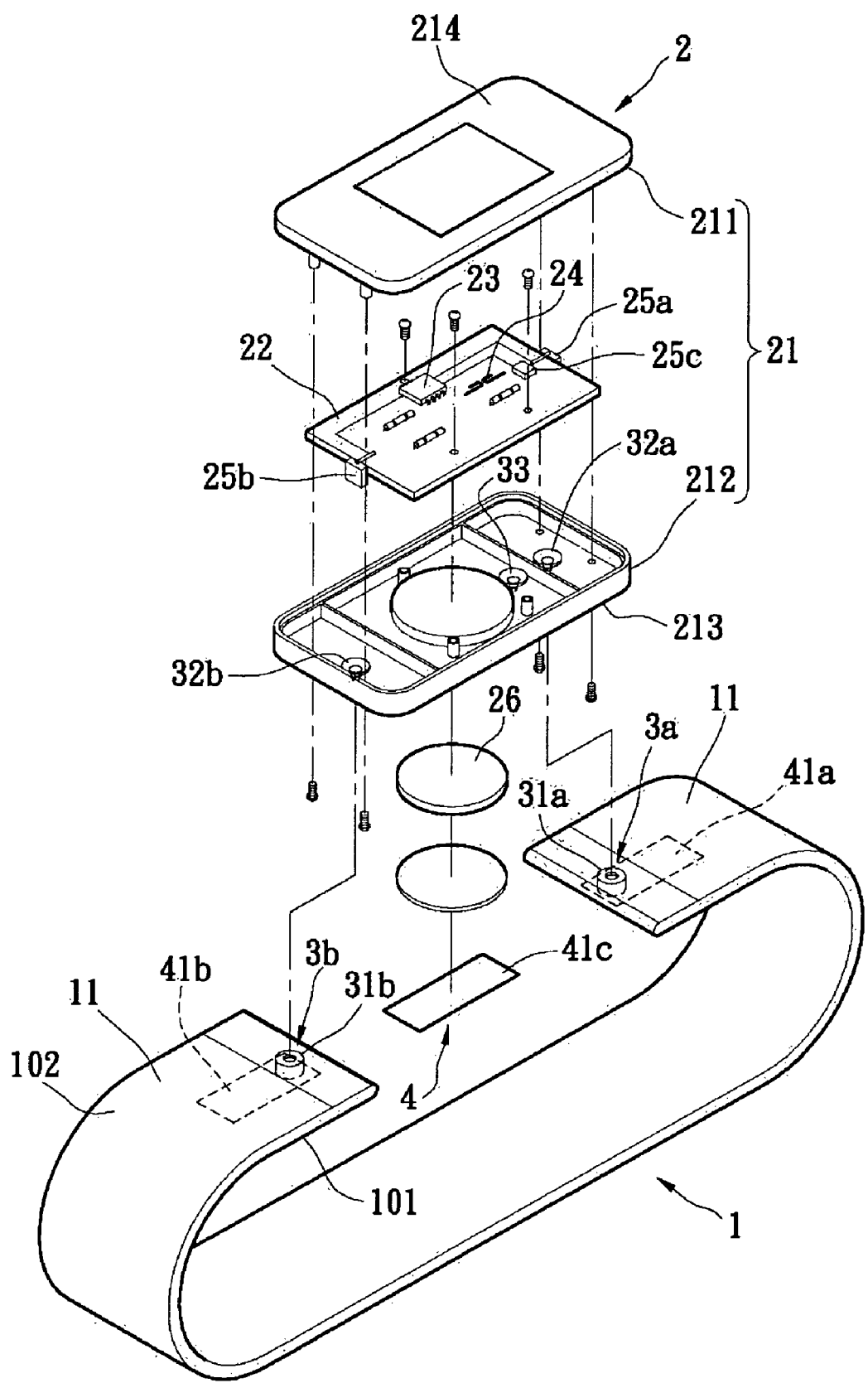
FIG. 1 is an exploded perspective view showing the first embodiment of the present invention.
Figure 2:
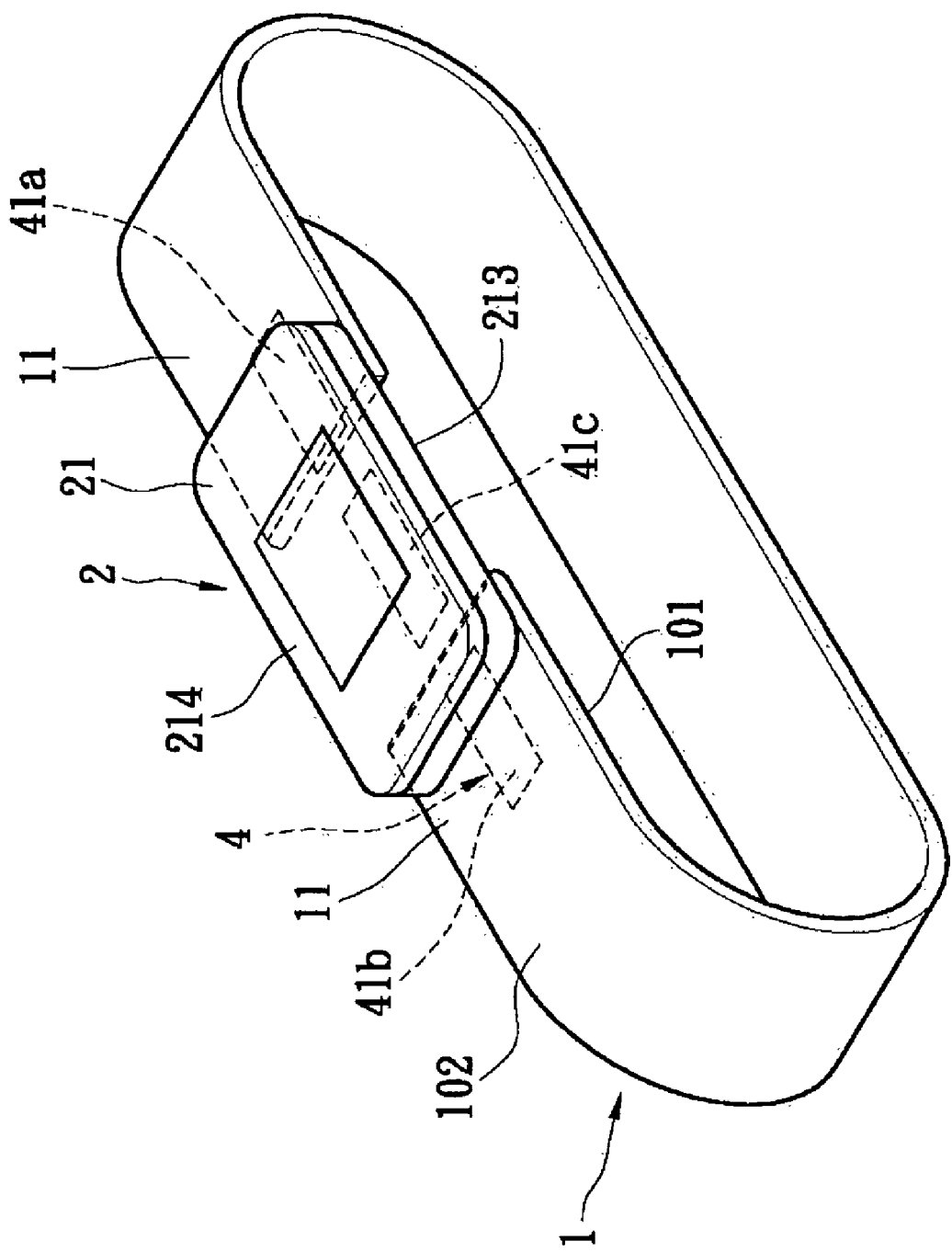
FIG. 2 is an assembled perspective view showing the first embodiment of the present invention.

Please refer to FIGS. 1 and 2. The present invention provides a wireless cardiogram signal diagnostic instrument, which comprises a band 1, a signal transmitting device 2, two sets of connecting pieces 3a, 3b, and a conductive assembly 4.

The band 1 is made of a soft insulating material and has a first surface 101 and a second surface 102 opposite to each other. Further, the band 1 has two mounting portions 11 opposite to each other and separated by a distance.

The signal transmitting device 2 comprises an outer casing 21, a circuit board 22, a signal transmitting element 23, an arithmetic processing element 24, a first electrode 25a, a second electrode 25b, and a third electrode 25c. The outer casing 21 has two shells 211, 212 assembled with each other. The outer casing 21 has a third surface 213 and a fourth surface 214 opposite to each other. The circuit board 22 is disposed within the outer casing 21. The signal transmitting element 23, the arithmetic processing element 24, the first electrode 25a, the second electrode 25b, and the third electrode 25c are all electrically connected to the circuit board 22 and electrically disposed thereon. Further, the signal transmitting device 2 comprises at least one power supplying element 26 that is electrically connected to the circuit board 22 for providing the necessary power.

The third surface 213 of the outer casing 21 of the signal transmitting device 2 is oriented in the same direction as that of the first surface 101 of the band 1, both of which belong to an inner surface. Conversely, the fourth surface 214 of the outer casing 21 is oriented in the same direction as that of the second surface 102 of the band 1, both of which belong to an outer surface.

The two sets of connecting pieces 3a, 3b each respectively has a first connecting piece 31a, 31b that are conductive and a second connecting piece 32a, 32b that are conductive, which can be a combination of a male fastener and a female fastener.

The conductive assembly 4 has a first conductive piece 41a, a second conductive piece 41b, and a third conductive piece 41c. The first and second conductive pieces 41a, 41b can be made of a soft conductive material such as conductive fabric. The third conductive piece 41c can be made of a metallic piece or a soft conductive material such as conductive rubber, or conductive fabric.

The first conductive piece 41a and the second conductive piece 41b are nakedly provided on the first surfaces 101 of the two mounting portions 11 of the band 1 respectively. The first connecting pieces 31a, 31b of the two sets of connecting pieces 3a, 3b are provided on the two mounting portions 11 of the band 1, and are electrically coupled to the corresponding first and second conductive pieces 41a, 41b. The second connecting pieces 32a, 32b are provided in the outer casing 21 of the signal transmitting device 2, and are electrically coupled to the corresponding first and second electrodes 25a, 25b. The third conductive piece 41c is nakedly provided between the first surfaces 101 of the band 1 and the third surface 213 of the outer casing 21. Further, the third conductive piece 41c is located between the two mounting portions 11 of the band 1, and is electrically coupled to the third electrode 25c by means of conductive medium such as leads, fasteners, or other conductive materials for conductive coupling.

Via this arrangement, the first connecting pieces 31a, 31b of the two sets of connecting pieces 3a, 3b can be assembled with the corresponding second connecting pieces 32a, 32b, so that the signal transmitting device 2 can be detachably assembled on the second surface 102 of the band 1.

Figure 3:
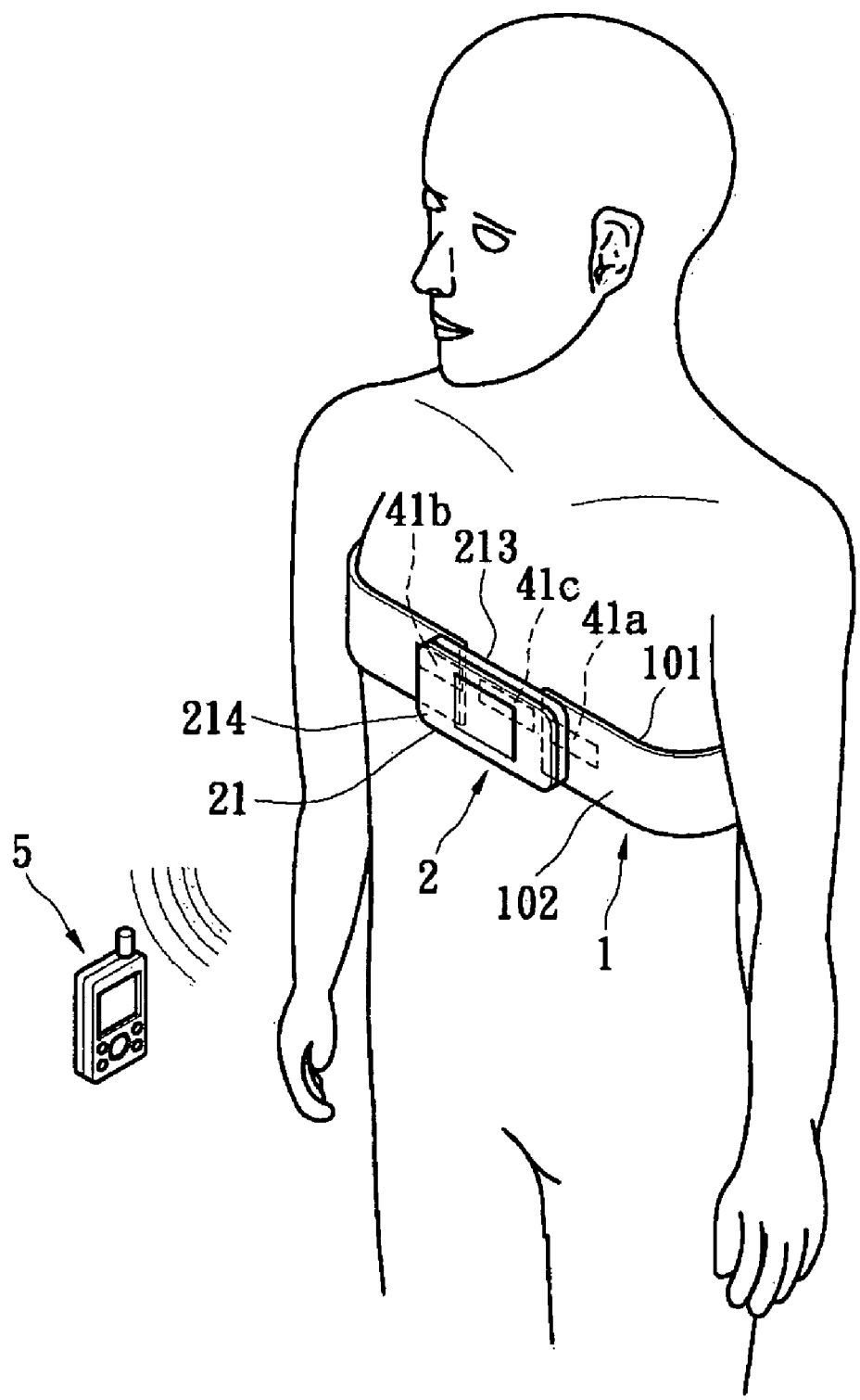
FIG. 3 is a schematic view showing the operating state of the present invention.

Please also refer to FIG. 3. In use, the band 1 is used to surround the user's chest with the first, second, and third conductive pieces 41a, 41b, 41c located in close proximity to the heart. Since the first and second conductive pieces 41a, 41b are located on the first surfaces 101 of the band 1, and the third conductive piece 41c is nakedly provided between the first surfaces 101 of the band 1 and the third surface 213 of the outer casing 21, these conductive pieces can be attached to the skin of the user so as to measure his/her potential signals. The potential signals measured by the first and second conductive pieces 41a, 41b can be transmitted to the first and second electrodes 25a, 25b via the two sets of connecting pieces 3a, 3b. On the other hand, the potential signals measured by the third conductive piece 41c can be transmitted to the third electrode 25c. Therefore, the variation values of cardiogram voltages measured by contacting the first to third conductive pieces 41a, 41b, 41c with the skin can be transmitted to the arithmetic processing element 24 via the first to third electrodes 25a, 25b, 25c for subsequent processing. After being processed, these variation values of cardiogram voltages are converted into digital signals of a cardiogram; Via the signal transmitting element 23, the digital signals are transmitted to a receiver 5 in a wireless manner, thereby displaying the cardiogram or recording the collected cardiogram signals. On the other hand, the receiver 5 can be held in a hand or hung on the user's waist, so that it is portable by the user. Therefore, it is very convenient for the user to monitor his/her cardiogram signals at any time.

Among the embodiments of the present invention, FIGS. 1 to 3 show a first embodiment of the present invention. The two mounting portions 11 of the band 1 are separated by a distance, that is, the two mounting portions are provided at a front end and a rear end of the band 1 respectively. The third conductive piece 41c is provided on the third surface 213 of the outer casing 21 of the signal transmitting device 2, and is electrically coupled with the third electrode 25c. On the other hand, with regard to the coupling between the third conductive piece 41c and the third electrode 25c, the present embodiment further comprises a third connecting piece 33 that is conductive, which is provided in the outer casing 21 of the signal transmitting device 2 and is electrically coupled to the third electrode 25c. The third connecting piece 33 is brought into electrical contact with the third conductive piece 41c, thereby achieving the electric coupling between the third conductive piece 41c and the third electrode 25c. In the first embodiment, the third conductive piece 41c can be made of different materials from that of the first and second conductive pieces 41a, 41b. For example, if the first and second conductive pieces 41a, 41b are made of conductive fabric, the third conductive piece 41c may be made of a metallic piece or a soft conductive material such as conductive rubber, or conductive fabric.

Figure 4:
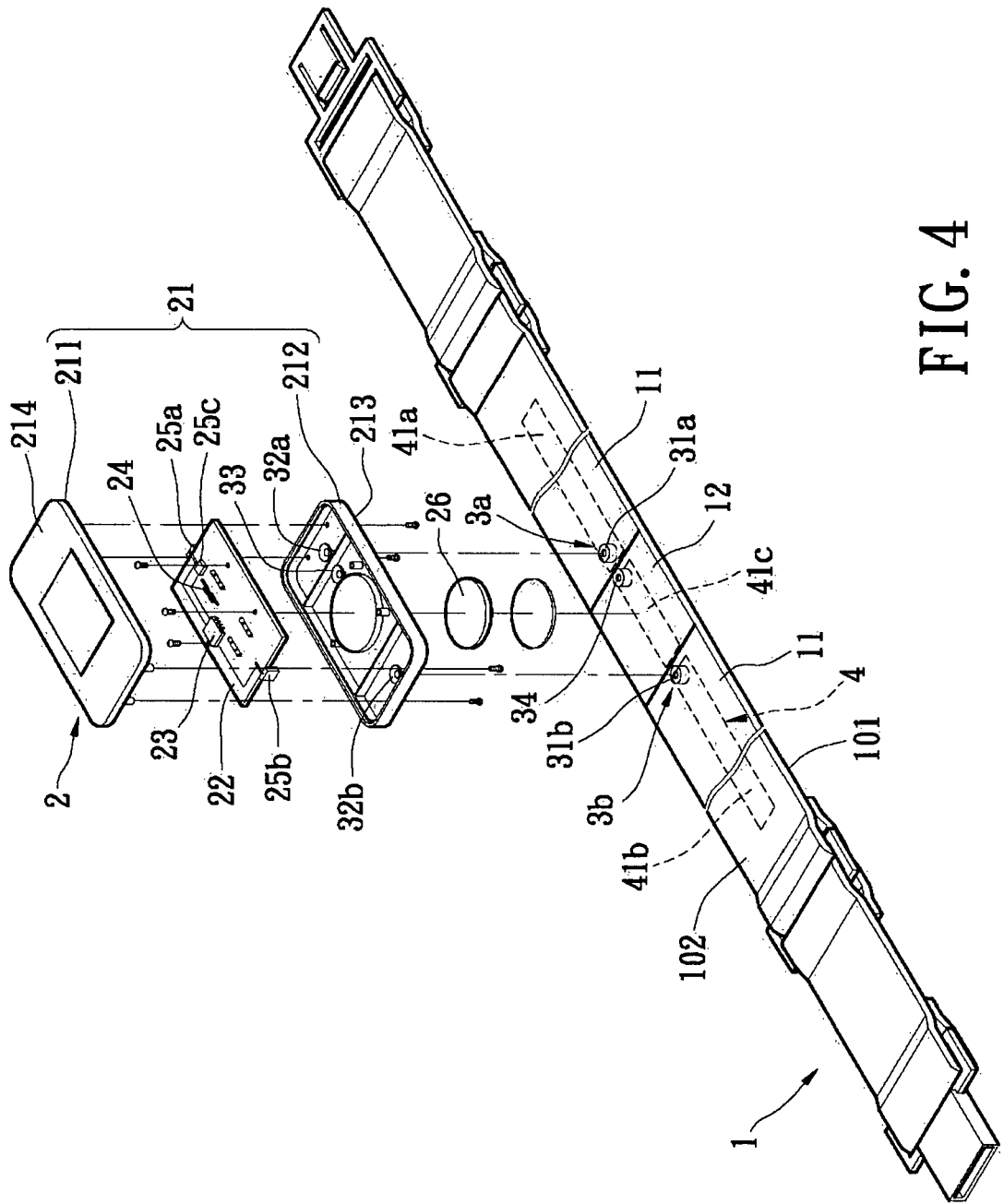
FIG. 4 is an exploded perspective view showing the second embodiment of the present invention.

In an alternative embodiment of the present invention, the signal transmitting device can be provided near the center of the band. Please refer to FIG. 4, which shows a second embodiment of the present invention. The difference between the second embodiment and the first embodiment lies in that: the band 1 is integrally connected with a middle portion 12 between the two mounting portions 11. That is, the mounting portions 11 are located near the center of the band 1 and connected with the middle portion 12. Similarly, the first and second conductive pieces 41a, 41b are nakedly provided on the first surfaces 101 of the two mounting portions 11. The two sets of connecting pieces 3a, 3b are also provided on the associated positions to thereby achieve the same effect. Thus, the repeated description is omitted for simplicity. The third conductive piece 41c is provided on the first surface 101 of the middle portion 12.

In the present embodiment, via the assembly of the first connecting pieces 31a, 31b and the second connecting pieces 32a, 32b of the two sets of connecting pieces 3a, 3b, the signal transmitting device 2 can be mounted on the band 1. At this time, the third conductive piece 41c is electrically coupled to the third electrode 25c of the signal transmitting device 2.

According to the above, the way of electrical coupling will be described in further detail hereafter. The embodiment of the present invention further comprises a third connecting piece 33 and a fourth connecting piece 34 that are conductive and can be assembled with each other. The third connecting piece 33 is also provided in the outer casing 21, and is electrically coupled to the third electrode 25c. The fourth connecting piece 34 is provided in the middle portion 12 of the band 1, and is electrically coupled to the third connecting piece 41c. Therefore, when the signal transmitting device 2 is mounted on the band 1 while the third connecting piece 33 and the fourth connecting piece 34 are assembled with each other, the third conductive piece 41c can be electrically coupled with the third electrode 25c. Via the above arrangement, the present embodiment can achieve the same effect as that of the previous embodiment. On the other hand, the third connecting piece 33 and the fourth connecting piece 34 can be a combination of a male fastener and a female fastener that can be assembled with each other. Next, the first to third conductive pieces 41a, 41b, 41c can be made of the same soft conductive material, such as conductive fabric.)

According to the above, the wireless cardiogram signal diagnostic instrument of the present invention can be worn on the user's chest with the first to third conductive pieces being attached to the user's skin, thereby located in close proximity to the user's heart so as to collect accurate variation values of cardiogram voltages. Then, the collected values are processed by the signal transmitting device and transmitted to a receiver. The transmitted signals are received by the receiver to display the cardiogram or record the collected cardiogram signals. Therefore, it is convenient for the user to monitor his/her cardiogram. Further, the drawback that the signals of a human body may be collected insufficiently or even lost can be solved.

While the present invention has been described in terms of what is presently considered to be the most practical and preferred embodiments, it is to be understood that the present invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A wireless cardiogram signal diagnostic instrument, comprising:
   a band having a first surface and a second surface opposite to each other, and having two opposite mounting portions separated by a distance;
   a signal transmitting device having an outer casing, a circuit board provided in the outer casing, and a signal transmitting element, an arithmetic processing element, a first electrode, a second electrode and a third electrode that are electrically connected to the circuit board, the outer casing having a third surface and a fourth surface opposite to each other, the third surface of the outer casing being oriented in the same direction as the first surface of the band, the fourth surface of the outer casing being oriented in the same direction as the second surface of the band;
   two sets of connecting pieces each having a first connecting piece and a second connecting piece that is conductive, the first connecting pieces being provided on the two mounting portions of the band and electrically coupled to a corresponding first conductive piece and a corresponding second conductive piece respectively, the second connecting pieces being provided on the outer casing of the signal transmitting device and electrically coupled to the corresponding first and second electrodes respectively, the first connecting pieces being assembled with the corresponding second connecting pieces so that the signal transmitting device is detachably assembled on the second surface of the band; and
   a conductive assembly having a first conductive piece, a second conductive piece, and a third conductive piece, the first and second conductive pieces being nakedly provided on the first surfaces of two mounting portions of the band, the third conductive piece being nakedly provided between the first surfaces of the band and the third surface of the outer casing with the third conductive piece being located between the two mounting portions, the third conductive piece and the third electrode being electrically coupled to each other;
   wherein the band further comprises a middle portion for integrally connecting the two mountins portions, the third conductive piece is provided on a first surface of the middle portion; and
   a third connecting piece that is conductive, and a fourth connecting piece that is conductive, the third connecting piece being provided on the outer casing of the signal transmitting device and electrically coupled to the third electrode, the fourth connecting piece being provided in the middle portion of the band and electrically coupled to the third conductive piece, the third connecting piece being assembled with the fourth connecting piece to thereby electrically couple the third conductive piece and the third electrode.

2. The wireless cardiogram signal diagnostic instrument according to claim 1, wherein the third conductive piece is provided on the third surface of the outer casing of the signal transmitting device to be electrically coupled to the third electrode.

3. The wireless cardiogram signal diagnostic instrument according to claim 1, further comprising a third connecting piece that is conductive, the third connecting piece being provided in the outer casing of the signal transmitting device and being electrically coupled to the third electrode, the third connecting piece being brought into electrical contact with the third conductive piece, thereby electrically coupling the third conductive piece to the third electrode.

4. The wireless cardiogram signal diagnostic instrument according to claim 1, wherein the third connecting piece and the fourth connecting piece are a combination of a male fastener and a female fastener that are assembled with each other.

5. The wireless cardiogram signal diagnostic instrument according to claim 1, wherein the signal transmitting device further comprises at least one power supplying element electrically connected to the circuit.

6. The wireless cardiogram signal diagnostic instrument according to claim 1, wherein the band is made of a soft insulating material.

7. The wireless cardiogram signal diagnostic instrument according to claim 1, wherein the first conductive piece and the second conductive piece are each made of a soft conductive material.

8. The wireless cardiogram signal diagnostic instrument according to claim 1, wherein the third conductive piece is made of a soft conductive material.

9. The wireless cardiogram signal diagnostic instrument according to claim 1, wherein the first connecting piece and the second connecting piece are a combination of a male fastener and a female fastener that are assembled with each other.

* * * * *